United States Patent
Lee et al.

(10) Patent No.: US 11,103,600 B2
(45) Date of Patent: Aug. 31, 2021

(54) HYDROGEL-BASED NANOENULSION FOR SELECTIVELY LABELING CANCER LESION, AND PREPARATION METHOD THEREFOR

(71) Applicant: SEOUL NATIONAL UNIVERSITY R&DB FOUNDATION, Seoul (KR)

(72) Inventors: Kang Won Lee, Suwon-si (KR); Yoon Jeong, Suwon-si (KR); Sara Lee, Suwon-si (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 356 days.

(21) Appl. No.: 16/314,624

(22) PCT Filed: Feb. 24, 2017

(86) PCT No.: PCT/KR2017/002069
§ 371 (c)(1),
(2) Date: Jan. 25, 2019

(87) PCT Pub. No.: WO2018/004105
PCT Pub. Date: Jan. 4, 2018

(65) Prior Publication Data
US 2020/0384128 A1    Dec. 10, 2020

(30) Foreign Application Priority Data

Jun. 29, 2016 (KR) .......................... 10-2016-0081254

(51) Int. Cl.
*A61K 49/00* (2006.01)
*A61K 47/36* (2006.01)
*A61K 49/18* (2006.01)

(52) U.S. Cl.
CPC .......... *A61K 49/0078* (2013.01); *A61K 47/36* (2013.01); *A61K 49/006* (2013.01); *A61K 49/0034* (2013.01); *A61K 49/0043* (2013.01); *A61K 49/1806* (2013.01); *A61K 49/1863* (2013.01)

(58) Field of Classification Search
CPC ................ A61K 49/0078; A61K 47/36; A61K 49/0034; A61K 49/0043; A61K 49/006; A61K 49/1806; A61K 49/1863; A61K 9/0014; A61K 9/1075; A61K 49/18; A61K 49/00; A61K 49/0019; G01N 33/57492; G01N 33/58; G01N 2800/50
See application file for complete search history.

(56) References Cited

U.S. PATENT DOCUMENTS

2001/0053376 A1   12/2001   Iwai et al.
2010/0062000 A1    3/2010   Turley et al.

FOREIGN PATENT DOCUMENTS

| CN | 1899264 A | 1/2007 |
|---|---|---|
| CN | 101626754 A | 1/2010 |
| CN | 102552174 A | 7/2012 |
| CN | 101878230 A | 11/2012 |
| JP | 2002-512942 T2 | 5/2002 |
| JP | 2010-235460 A | 10/2010 |
| KR | 10-0825944 B1 | 4/2008 |
| KR | 10-2009-0097582 A | 9/2009 |
| KR | 10-2009-0121848 A | 11/2009 |
| WO | 98/23293 A1 | 6/1998 |
| WO | 08/100044 A1 | 8/2008 |
| WO | 2009/077399 A1 | 6/2009 |
| WO | 2018/004105 A1 | 2/2017 |

OTHER PUBLICATIONS

Korean Application No. 16-81254 received an Office Action, dated Jan. 12, 2018, 4 pages.
Korean Application No. 16-81254 a Notice of Allowance, dated Oct. 15, 2018, 2 pages.
Subbiah, Ramesh, "Development of Contrast Agents for the Selective Labeling for Cancerous Lesions using a Hydrogel-based Nanoemulsions", Apr. 2016 53-53, 1 page.
Xing, Zhimin, et. al. "Dual stimuli responsive hollow nanogels with IPN structure for temperature controlling drug loading and pH triggering drug release", Jul. 7, 2011, 6 pages.
International PCT Application No. PCT/KR2017/002069 received a Written Opinion, dated Jun. 7, 2017, 4 pages.
International PCT Application No. PCT/KR2017/002069 received an International Search Report, dated Jun. 7, 2017, 5 pages.
Chung-Wook, Chung, "Interpenetrating polymer network (IPN) scaffolds of sodium hyaluronate and sodium alginate for chondrocyte culture", Colloids and Surfaces B: Biointerfaces 88 (2011) 711-716, 6 pages.
Lee, Fan et. al. "Formation and stability of interpenetrating polymer network hydrogels consisting of fibrin and hyaluronic acid for tissue engineering", Acta Biomaterialia 9 (2013) 5143-5152, 10 pages.
Chavanpatil, et al., "Polymer-Surfactant Nanoparticles for Sustained Release of Water-Soluble Drugs," Journal of Pharmaceutical Sciences, 2007, vol. 96, No. 12, p. 3379-3389.
Jeong, et al., Proceeding of the Polymer Society of Korea Conference, Mar. 31, 2016, p. 53.
Kong, et al., "Investigations on skin permeation of hyaluronic acid based nanoemulsion as transdermal carrier," Carbohydrate Polymers vol. 86 (2011) 837-843.
Vongcharoe, Pattarawadee, "Formulation, characterization and stability evaluation of virgin coconut oil (VCO) enriched hyaluronic acid based emulsion," Jan. 1, 2016, Thesis pp. 1-96.
Wang, et al., "In vivo lymphatic targeting of methylene blue with microemulsion and multiple microemulsion," Drug Delivery, vol. 16, No. 7, Jul. 7, 2009, pp. 371-377.
Extended European Search Report for EP 17 820 382.4 dated May 28, 2019, 8 pages.
The First Office Action for CN201780049467.7 dated Dec. 25, 2020, all pages.

*Primary Examiner* — Robert S Cabral
(74) *Attorney, Agent, or Firm* — Kilpatrick Townsend & Stockton LLP (57) ABSTRACT

One embodiment of the present invention relates to a nanoemulsion and a preparation method therefor, the nanoemulsion comprising an oil component, a surfactant, and an aqueous component, wherein the aqueous component comprises a water-soluble active ingredient, a polysaccharide, and hyaluronic acid.

10 Claims, 13 Drawing Sheets

| Sample | Oil phase | Co-surfactant (Span 80 / Tween 80) | Aqueous phase |
|---|---|---|---|
| NE 6 | 3.5 | 0.42 / 0.08 | 0.25 / 0.25 / 0.5 = HA 0.5wt% / Alg 0.5wt% / MB 0.1mM |
| NE 7 | 3.5 | 0.37 / 0.13 | 0.25 / 0.25 / 0.5 = HA 0.5wt% / Alg 0.5wt% / MB 0.1mM |
| NE 8 | 3.5 | 0.32 / 0.18 | 0.25 / 0.25 / 0.5 = HA 0.5wt% / Alg 0.5wt% / MB 0.1mM |
| NE 9 | 3.5 | 0.28 / 0.22 | 0.25 / 0.25 / 0.5 = HA 0.5wt% / Alg 0.5wt% / MB 0.1mM |

(% w/w)

In order to calculate how much of Tween 80 (A) is blended with Span 80 (B) to attain a given HLB value of X, the following equation can be utilised:

$$\%(A) = \frac{(X - HLB) \times 100}{HLB - HLB} \quad \%(B) = 100 - \%(A)$$

HYDROGEL-BASED NANOEMULSION FOR SELECTIVELY LABELING CANCER LESION, AND PREPARATION METHOD THEREFOR

TECHNICAL FIELD

The present disclosure relates to a hydrogel-based nanoemulsion for selective labeling of cancerous lesions, and a preparation method the same.

BACKGROUND ART

Diagnosis of dysplasia and early-stage cancer using general contrast agents is difficult because of the unclear boundaries of lesions, and there have been difficulties in accurate diagnosis of a cancerous lesion by performing a random biopsy on a suspicious site. Therefore, advances in surgical assistive technologies have been made to accurately detect a lesion in real time and to effectively indicate a resection area during surgical procedures.

Accordingly, a staining technique that enables selective adsorption to cancerous lesions has been needed for easier and more accurate diagnosis of cancer during surgical procedures or diagnostic procedures using medical equipment. Due to such technical demands, studies are being conducted on nanoparticles or compositions to develop a staining agent that is selective for cancerous lesions of the human body or targets cancer cells.

CITATION LIST

PATENT LITERATURE 1: Korean Patent Publication No. 2009-0097582

DESCRIPTION OF EMBODIMENTS

Technical Problem

An aspect of the present disclosure provides a nanoemulsion for selective labeling of cancerous lesions of the human body and for effective delivery of a cancer cell-targeting staining agent to cancerous lesions, the nanoemulsion enabling a physician to perform accurate diagnosis and treatment during surgical procedures or diagnostic procedures using medical equipment in cancer treatment, and a method of preparing the nanoemulsion.

Solution to Problem

An aspect of the present disclosure provides a nanoemulsion including an oil component; a surfactant; and an aqueous component wherein the aqueous component includes a water-soluble active ingredient; a polysaccharide; and a hyaluronic acid.

Further, the nanoemulsion may include an interpenetrating polymer network structure consisting of the water-soluble active ingredient, the polysaccharide, and the hyaluronic acid.

In one embodiment of the present disclosure, the nanoemulsion may have an average particle size of 200 nm or less.

In another embodiment of the present disclosure, the nanoemulsion is a water-in-oil-type emulsion.

Further, the nanoemulsion may include 70% by weight to 80% by weight of the oil component, 10% by weight to 20% by weight of the aqueous component, and 5% by weight to 15% by weight of the surfactant, based on the total weight of the nanoemulsion.

The surfactant may include at least one of a single surfactant and a co-surfactant.

In one embodiment of the present disclosure, nanoparticles included in the nanoemulsion may have an average particle size distribution of 0.2 to 0.7 and a zeta potential of −20 mV to −50 mV.

In one embodiment of the present disclosure, the polysaccharide may be alginate.

In one embodiment of the present disclosure, the water-soluble active ingredient may be a water-soluble stain or a water-soluble drug.

Specifically, the water-soluble stain may be any one selected from the group consisting of methylene blue, indigo carmine, Lugol solution, toluidine blue, congo red, phenol red, indocyanine green, fluorescein sodium, and India ink, and a concentration of the water-soluble stain may be 1 mM to 10 mM.

Further, a hydrophilic-lipophilic balance value of the nanoemulsion of the present disclosure is 6 to 9, which is favorable in terms of size control of the nanoemulsion.

Further, the present disclosure provides a method of preparing the above-described nanoemulsion, the method including preparing an oil component; preparing a surfactant; preparing an aqueous component; and mixing and stirring the oil component, the surfactant, and the aqueous component, wherein the aqueous component includes a water-soluble active ingredient, a polysaccharide, and a hyaluronic acid.

Lastly, the method of preparing the above-described nanoemulsion may include preparing the aqueous component, wherein the preparing of the aqueous component may include preparing a first aqueous component including the polysaccharide and the hyaluronic acid; and preparing a second aqueous component including the water-soluble active ingredient, wherein a weight ratio of the first aqueous component to the second aqueous component is 1:0.5 to 1:2.

Advantageous Effects of Disclosure

Use of a nanoemulsion according to an aspect of the present disclosure may greatly contribute to activation of early diagnosis of cancers using contrast agents.

Further, by efficiently delivering a staining agent for selective labeling of cancer to the human body, it is possible to maximize therapeutic effects on cancer through accurate diagnosis of a cancerous lesion by a physician and effective resection during surgical procedures as well as early detection of cancer.

Further, cancer treatment and symptom relief as well as cancer diagnosis may be expected by controlling an active ingredient of the nanoemulsion.

The nanoemulsion according to an aspect of the present disclosure is a formulation which may be commercialized through preclinical and clinical trials, and thus has an advantage of being mass-produced by a relatively simple preparation method.

The nanoemulsion prepared by a method of preparing the nanoemulsion according to an aspect of the present disclosure may have homogeneity, thereby providing nanoparticles having excellent thermodynamic stability.

BEST MODE

Hereinafter, the present disclosure will be descried in more detail.

Unless defined otherwise, all technical terms used herein have the same meaning as those generally understood by one of ordinary skill in the art to which the present disclosure belongs. Further, any methods or materials similar or equivalent to those described herein are also within the scope of the present disclosure. Also, the numerical values used herein are considered to include the meaning of "about" unless explicitly stated. It will be understood that the term "including" in the description means that a corresponding element may be included, and other elements may be further included rather than other elements being excluded unless content to the contrary is specially described. The disclosures of all articles cited herein are hereby incorporated, by reference, in their entireties.

An aspect of the present disclosure provides a nanoemulsion including an oil component; a surfactant; and an aqueous component, wherein the aqueous component includes a water-soluble active ingredient; a polysaccharide; and a hyaluronic acid.

As used herein, the "oil component" may refer to a lipid-soluble substance which is solubilized in oil. In the present disclosure, the oil component may be soybean oil.

As used herein, the "aqueous component" may refer to a water-soluble substance which is solubilized in water. In the present disclosure, the aqueous component may include a water-soluble active ingredient; a polysaccharide; and a hyaluronic acid.

As used herein, the "emulsion" refers to a state in which an aqueous component and an oil component not miscible with each other are dispersed, and includes an oil-in-water (O/W-type) emulsion and its opposite water-in-oil (W/O-type) emulsion. The nanoemulsion of the present disclosure may refer to an emulsion including nanoparticles consisting of a water-soluble active ingredient; a polysaccharide; and a hyaluronic acid.

Figure 2:
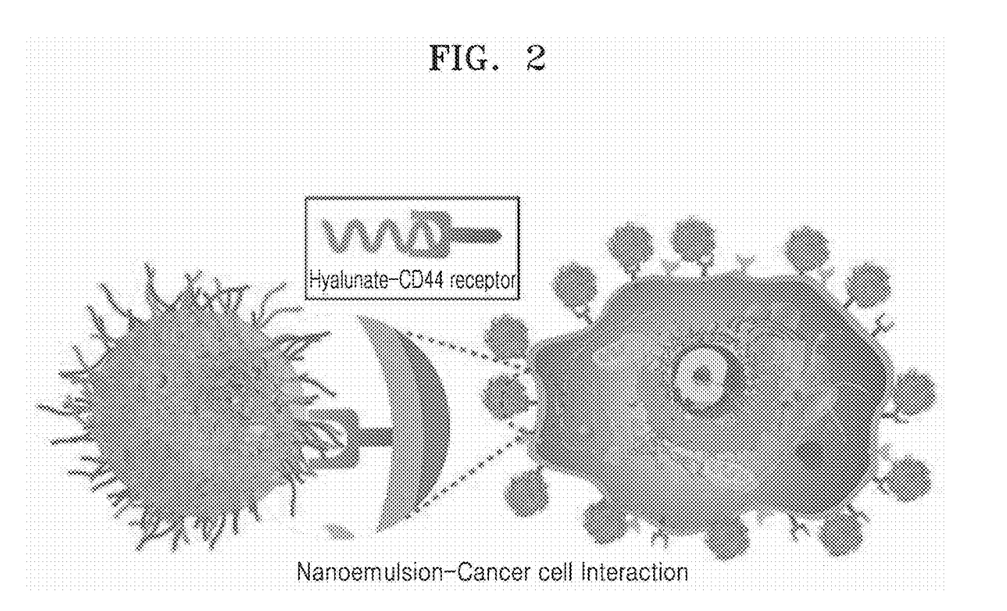
FIG. 2 illustrates cancer cell-nanoemulsion interaction.

In the present disclosure, the hyaluronic acid may play a role in internalization of the active ingredient of the nanoemulsion into cancer cells of a cancerous lesion via interaction with CD44 receptors overexpressed in the cancer cells. In this case, for cancer resection, a water-soluble active ingredient such as methylene blue is topically administered and selectively adsorbed onto the cancerous lesion to guide precise control of ablation during surgery. FIG. 2 shows cancer cell-nanoemulsion interaction.

In one embodiment of the present disclosure, the polysaccharide may be an anionic polysaccharide or a cationic polysaccharide.

Specifically, in the present disclosure, the polysaccharide may refer to all polysaccharides existing in nature, excluding synthetic compounds, and the polysaccharide may be, for example, cellulose, pectin, chitin, beta-glucan, etc., but is not limited thereto.

In one embodiment of the present disclosure, when the polysaccharide is an anionic polysaccharide, the nanoemulsion may be prepared by including a cationic aqueous contrast agent or a cationic material. In another embodiment of the present disclosure, when the polysaccharide is a cationic polysaccharide, the nanoemulsion may be prepared by including an anionic aqueous contrast agent or an anionic material.

In one embodiment of the present disclosure, the polysaccharide is alginate. In the present disclosure, the alginate may be a copolymer chain consisting of mannuronic acid (M) block and guluronic acid (G) block, and generally extracted from seaweeds.

In one embodiment of the present disclosure, the water-soluble active ingredient may be a water-soluble stain or a water-soluble drug.

Specifically, the water-soluble stain may be any one selected from the group consisting of indigo carmine, methylene blue, Lugol solution, toluidine blue, congo red, phenol red, indocyanine green, fluorescein sodium, and india ink, but is not limited thereto. Any stain used in chromoscopy in the art may be used.

Further, in the present disclosure, the water-soluble drug may be a necessary drug used in the art, but is not limited thereto.

In one embodiment of the present disclosure, the nanoemulsion may include nanoparticles having an interpenetrating polymer network structure consisting of the water-soluble active ingredient, polysaccharide, and hyaluronic acid.

As used herein, the interpenetrating polymer network structure may refer to an entangled network formed by two or more components without covalent bonds. In the interpenetrating polymer network structure according to the present disclosure, the water-soluble active ingredient is physically encapsulated, thereby increasing mechanical strength and thermodynamic stability.

Figure 1:
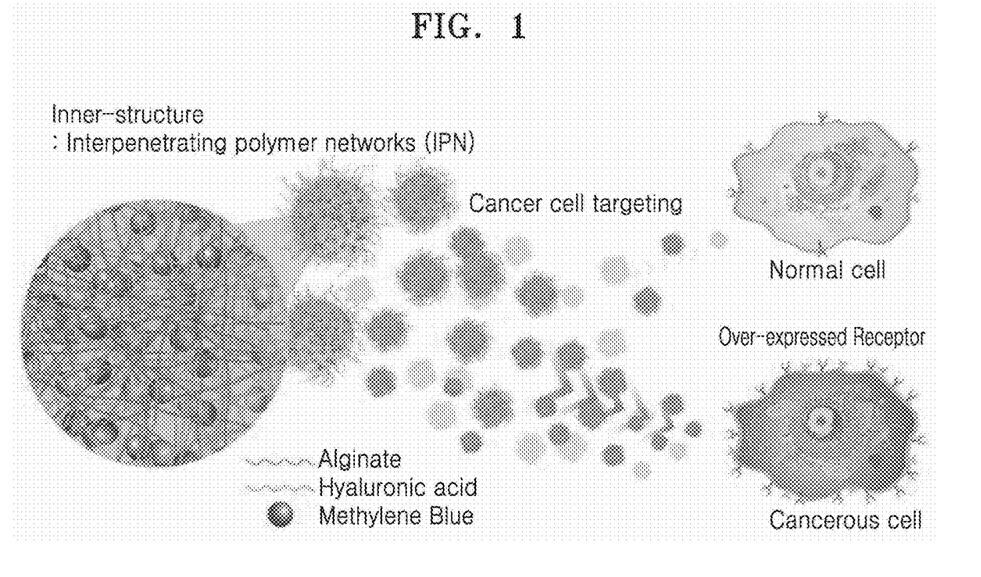
FIG. 1 illustrates an interpenetrating polymer network structure consisting of a water-soluble active ingredient, a polysaccharide, and a hyaluronic acid, together with cancer targeting by nanoparticles.

FIG. 1 illustrates the interpenetrating polymer network structure consisting of the water-soluble active ingredient, the polysaccharide, and the hyaluronic acid, together with cancer targeting by the nanoemulsion.

FIG. 2 illustrates cancer cell-nanoemulsion interaction. Specifically, binding between two materials is attributed to specific interactions between a chain structure present in hyaluronic acid and CD44 receptors overexpressed in cancer cells.

Figure 3:
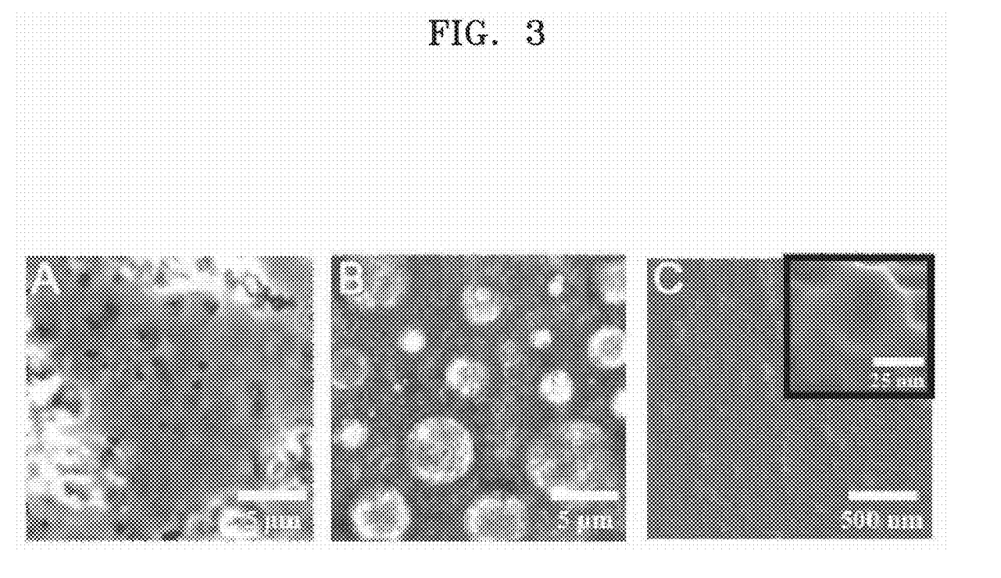
FIG. 3 shows an image obtained by optical microscopy before particle preparation, and an image obtained by scanning electron microscopy after particle preparation.

FIG. 3 shows an image obtained by optical microscopy (A) before particle preparation, an image obtained by optical microscopy (B) of micro-sized particles when vortexed, and an image of scanning electron microscopy (C) of nanoparticles prepared by sonication.

Figure 4:
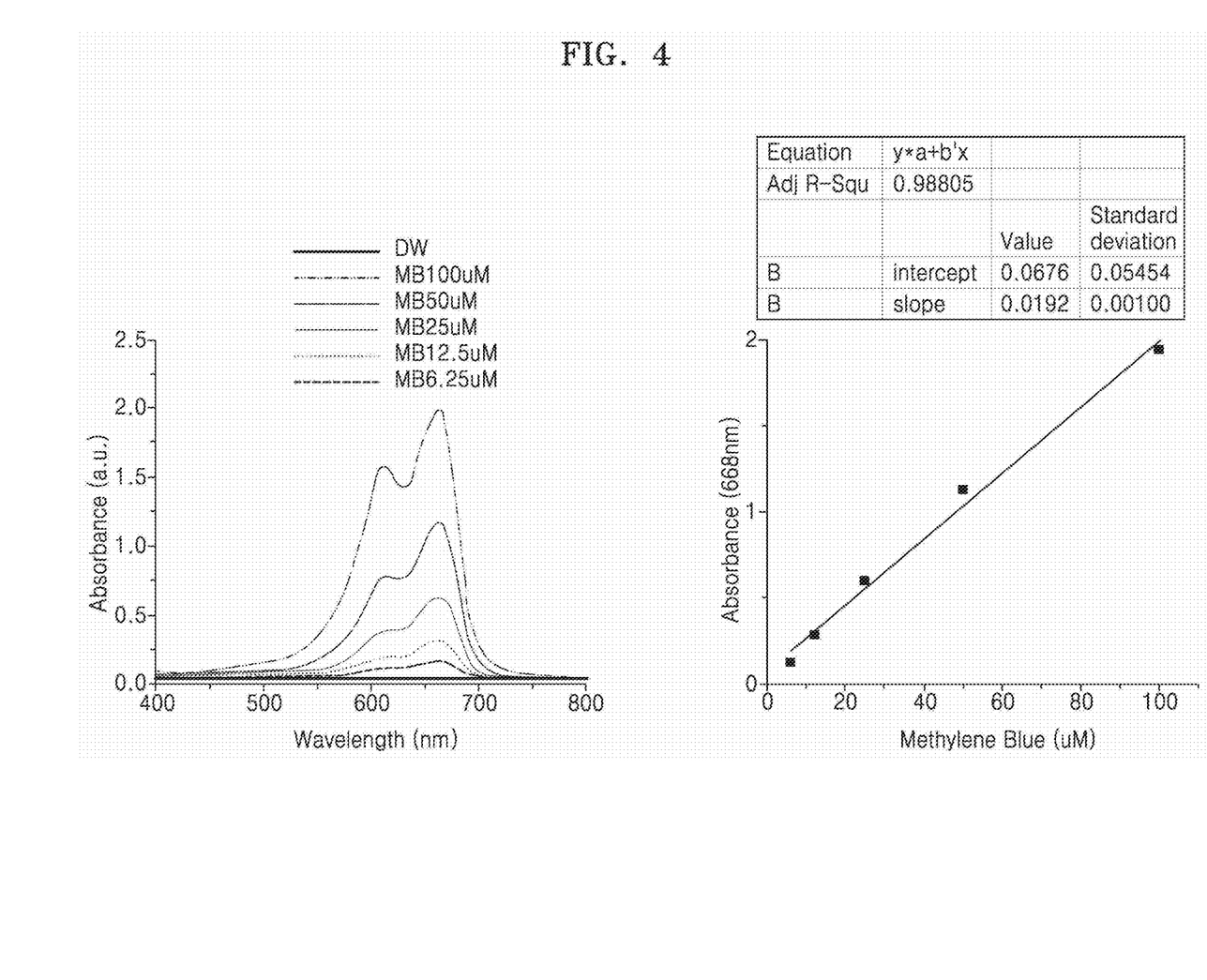
FIG. 4 shows absorbance according to methylene blue concentrations, and a linear relationship between absorbance and methylene blue concentration.

FIG. 4 shows absorbance according to methylene blue concentrations (right) and a linear relationship between absorbance and methylene blue concentration (left). Specifically, in FIG. 4, after measuring absorbance according to methylene blue concentrations, the absorbance of nanoparticles is compared with a standard concentration to predict the nanoemulsion concentration and methylene blue loading efficiency.

Figure 10:
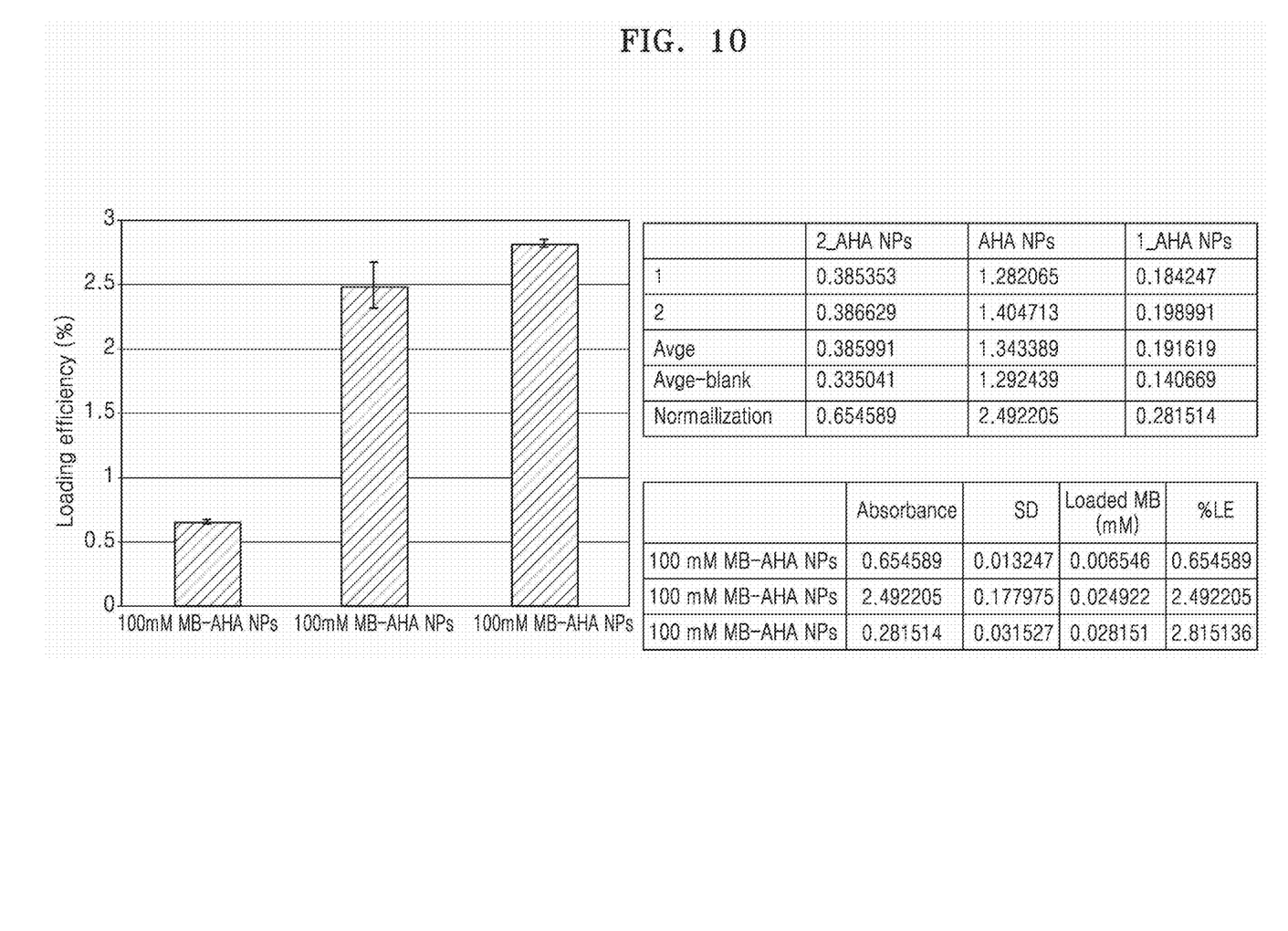
FIG. 10 shows methylene blue loading efficiency.

FIG. 10 shows prediction of methylene blue loading efficiency. From the results, loading efficiency of the methylene blue inside the nanoparticles included in the nanoemulsion may be predicted.

Figure 5:
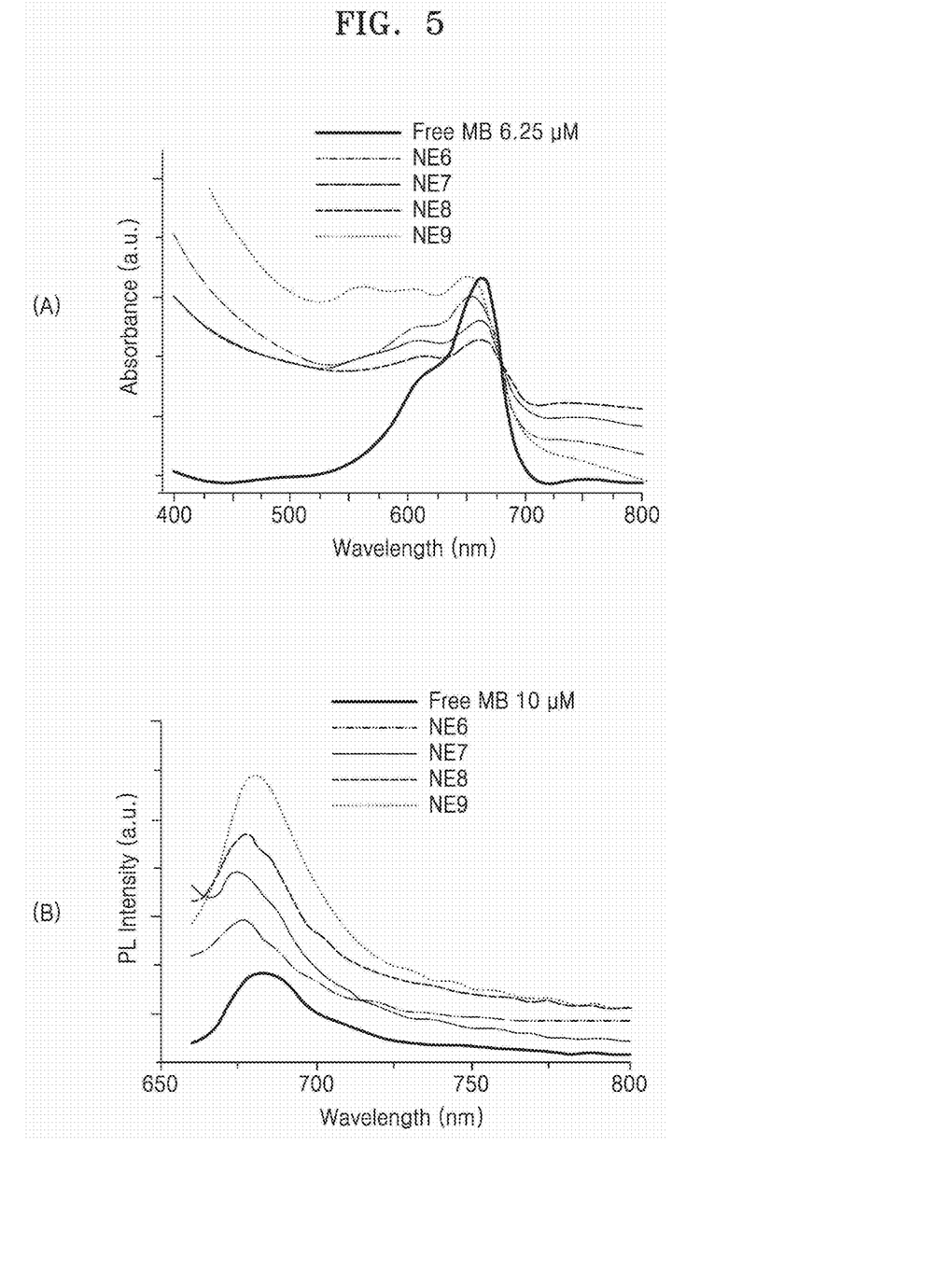
FIG. 5 shows absorbance (A) of methylene blue and nanoemulsions, and a fluorescence spectrum (B) obtained by a spectrofluorometer.

FIG. 5 shows absorbance of methylene blue and nanoemulsion, and fluorescence spectrum obtained by a spectrofluorometer. Specifically, the absorbance results in the left of FIG. 5 show that methylene blue has a fluorescence peak at a wavelength of 668 nm, and the graph in the right of FIG. 5 shows that the nanoemulsion including nanoparticles also has a fluorescence peak near a wavelength of 668 nm, indicating that methylene blue is included inside the nanoparticles. With regard to the prepared nanoemulsion, the peak shift to the left (blue-shift) may be attributed to difference of electrostatic complexes present inside the nanoemulsion. Further, the presence of methylene blue may be confirmed by the wavelength of the peak in the fluorescence spectrum.

Figure 9:
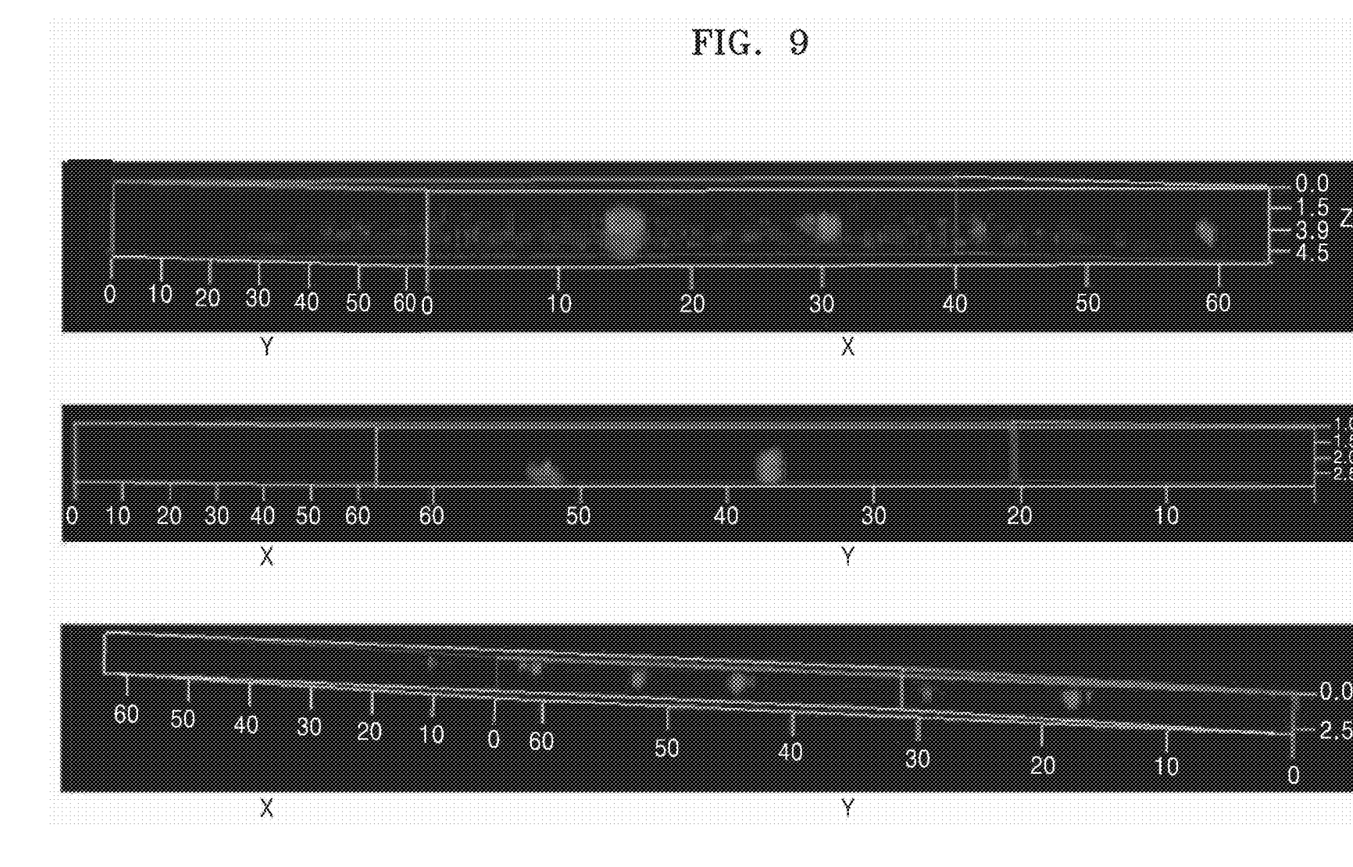
FIG. 9 is an image showing morphology of a nanoemulsion measured using confocal microscopy.

FIG. 9 is an image showing morphology of the nanoemulsion measured using confocal microscopy. The result of FIG. 9 shows that the methylene blue particles are included in the nanoemulsion.

In one embodiment of the present disclosure, the nanoemulsion may have an average particle size of 200 nm or less.

The nanoparticles included in the nanoemulsion of the present disclosure may have an average particle size distribution of 0.2 to 0.7. When the nanoparticles has the above particle size distribution, a nanoemulsion including nanoparticles having homogeneity may be provided. In terms of homogeneity of the nanoparticles, the nanoparticles may have an average particle size distribution of 0.2 to 0.4.

In one embodiment of the present disclosure, the nanoemulsion may have a zeta potential of −20 mV to −50 mV. The zeta potential of the nanoemulsion of the present disclosure is a value resulting from negative charge values of alginate and hyaluronic acid in an aqueous solution. When the nanoemulsion has a zeta potential in the above range, a phenomenon such as Ostwald ripening may be prevented, thereby providing a nanoemulsion including stable nanoparticles. In terms of stability of the nanoparticles, the nanoemulsion may have a zeta potential of −20 mV to −40 mV.

In another embodiment of the present disclosure, the nanoemulsion may be a water-in-oil-type emulsion.

Further, the nanoemulsion may include 70% by weight to 80% by weight of the oil component, 10% by weight to 20% by weight of the aqueous component, and 5% by weight to 15% by weight of the surfactant, based on the total weight of the nanoemulsion. The surfactant may include at least one of a single surfactant and a co-surfactant.

Within the above content range, the size of the nanoemulsion may be controlled in a desired range, and particles may have excellent stability.

Figure 6:
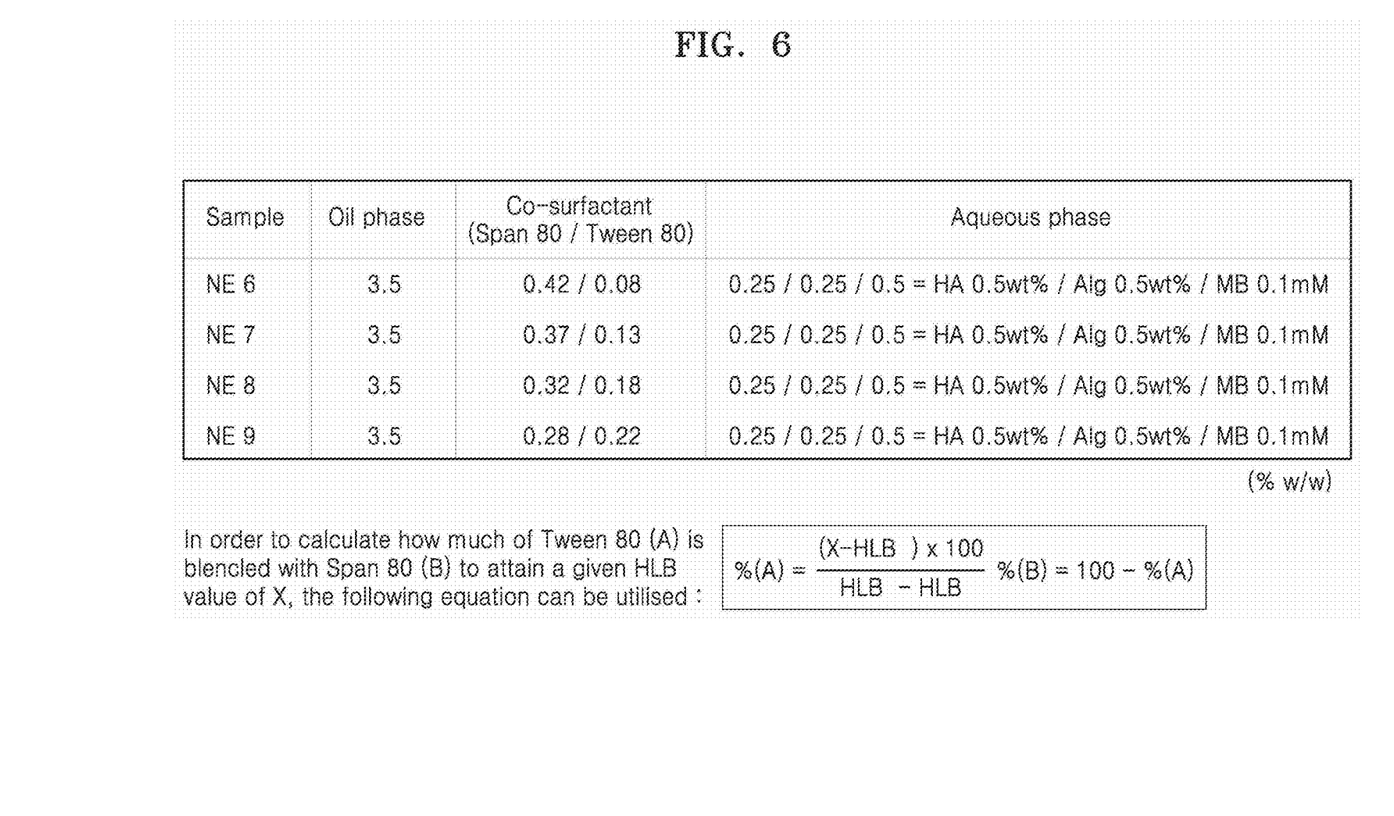
FIG. 6 shows an equation for the preparation of a co-surfactant, and a content ratio thereof for the preparation of a nanoemulsion.

In still another embodiment of the present disclosure, when nano-sized particles are prepared by mixing two or more surfactants, a co-surfactant may be used. FIG. 6 shows exemplary preparation and an equation to obtain a hydrophilic-lipophilic balance value of the co-surfactant based on intrinsic hydrophilic-lipophilic balance values of surfactants. In one embodiment of the present disclosure, Tween 80 (HLB value: 15) and Span 80 (HLB value: 4.3) were used. The two kinds of the surfactants were mixed at a predetermined weight ratio, and then the hydrophilic-lipophilic balance value of the co-surfactant was adjusted.

In still another embodiment of the present disclosure, % by weight of the aqueous component is larger than % by weight of the surfactant, based on the total weight of the nanoemulsion. In this case, nano-sized particles may be provided, and stability of the particles are excellent.

Further, the hydrophilic-lipophilic balance value of the co-surfactant used in the preparation of the nanoemulsion of the present disclosure may be 6 to 9 in terms of controlling the size of the nanoemulsion. The hydrophilic-lipophilic balance value of the nanoemulsion of the present disclosure may be 6 to 9 in terms of controlling the size of the nanoemulsion.

As used herein, the hydrophilic-lipophilic balance is a measure of the degree of hydrophilicity and lipophilicity, and a surfactant has an intrinsic hydrophilic lipophilic balance (HLB) value between 0 to 20. An HLB value closer to 0 is more lipophilic and an HLB value closer to 20 is more hydrophilic.

FIG. 6 shows a preparation ratio of nanoemulsion according to a hydrophilic-lipophilic balance value. Specifically, the nanoemulsion in FIG. 6 is a nanoemulsion prepared by using oil component:co-surfactant:aqueous component at a weight ratio of 7:1:2.

Further, the present disclosure provides a method of preparing the above-described nanoemulsion, the method including preparing an oil component; preparing a surfactant; preparing an aqueous component; and mixing and stirring the oil component, the surfactant, and the aqueous component, wherein the aqueous component includes a water-soluble active ingredient, a polysaccharide, and a hyaluronic acid. The surfactant may include at least one of a single surfactant and a co-surfactant.

In still another embodiment of the present disclosure, the preparing of the aqueous component may include preparing a first aqueous component including the polysaccharide and the hyaluronic acid; and preparing a second aqueous component including the water-soluble active ingredient.

In one embodiment of the present disclosure, the mixing and stirring of the oil component, the surfactant, and the aqueous component may be performed by sonication.

Figure 7:
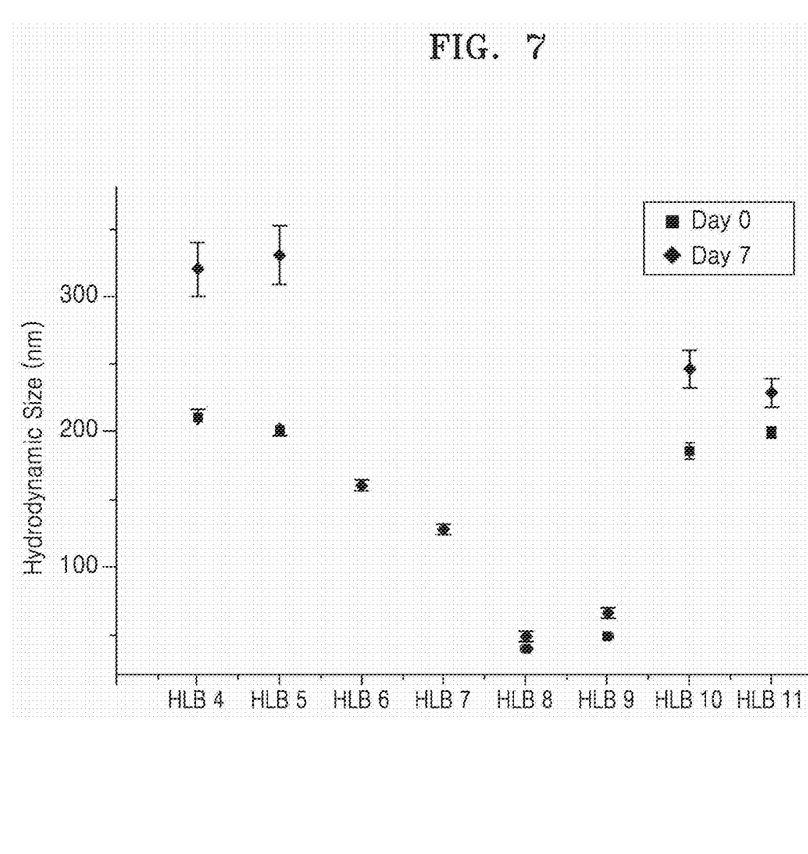
FIG. 7 shows a comparison of nanoemulsion size according to hydrophilic-lipophilic balance values.

FIG. 7 shows results of measuring size and thermodynamic stability of particles prepared according to HLB values of surfactants in the preparation of nanoemulsions.

The results show that when the HLB value of the surfactant used in the preparation of nanoemulsion is 6 to 7, the particle size did not increase after 1 week, indicating that thermodynamic stability of the particles may be maintained. It was found that when the HLB value of the surfactant is 8 to 9, particles had the smallest size, and but stability of particles may not be maintained. It was found that when the HLB value is 4 to 5 and 10 to 11, prepared particles had a relatively large size and particle stability may not be secured.

Figure 8:
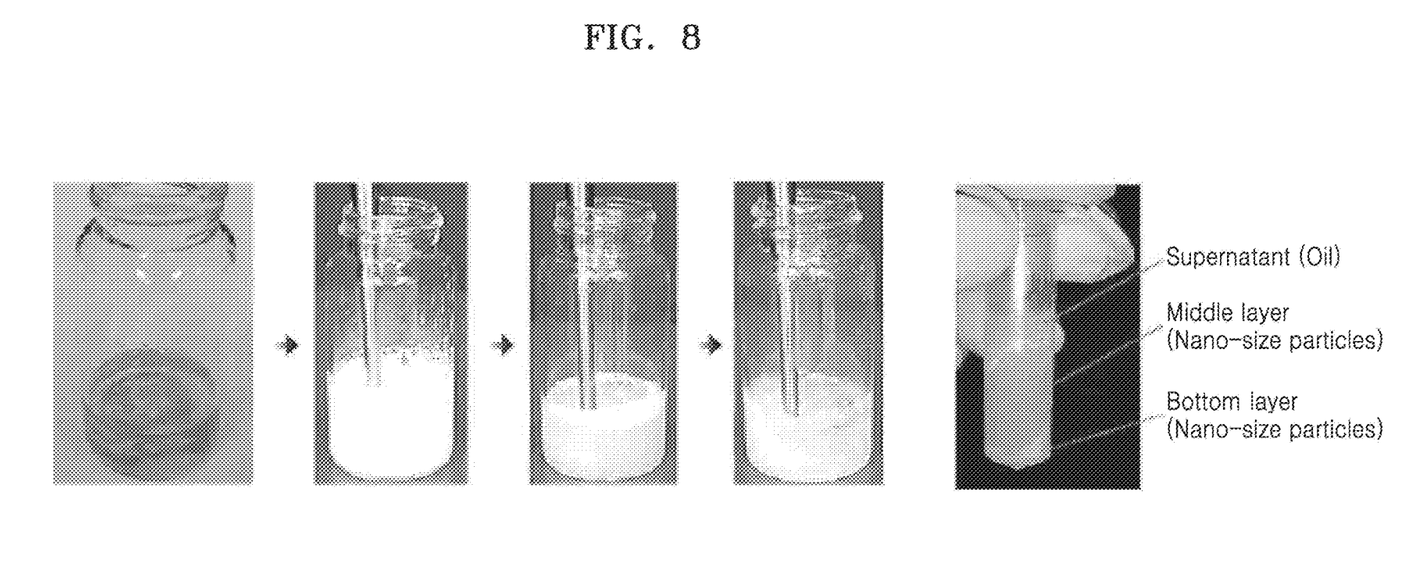
FIG. 8 shows procedures for preparation of a nanoemulsion, and phase separation of a nanoemulsion after centrifugation and before filtration.

FIG. 8 shows procedures for preparation of the nanoemulsion, and phase separation of the nanoemulsion after centrifugation and before filtration. Specifically, an oil component including a surfactant was mixed with an aqueous component including a first aqueous component and a second aqueous component, and then nanoparticles were prepared using a tip-shaped sonicator. After sonication, the aqueous component includes nanoparticles, and therefore, separated using a centrifuge, and filtered to obtain a nanoemulsion.

Figure 11:
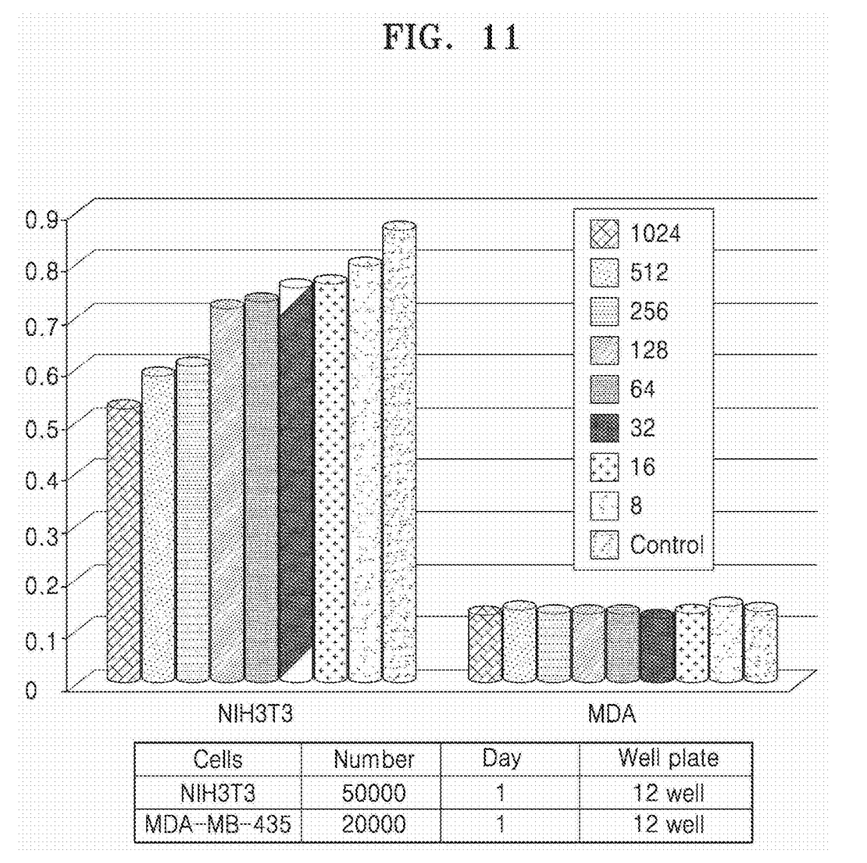
FIG. 11 shows a cell viability test.

FIG. 11 shows a cell viability test. The results of FIG. 11 confirmed that the nanoemulsion of the present disclosure has no cytotoxicity.

Figure 12:
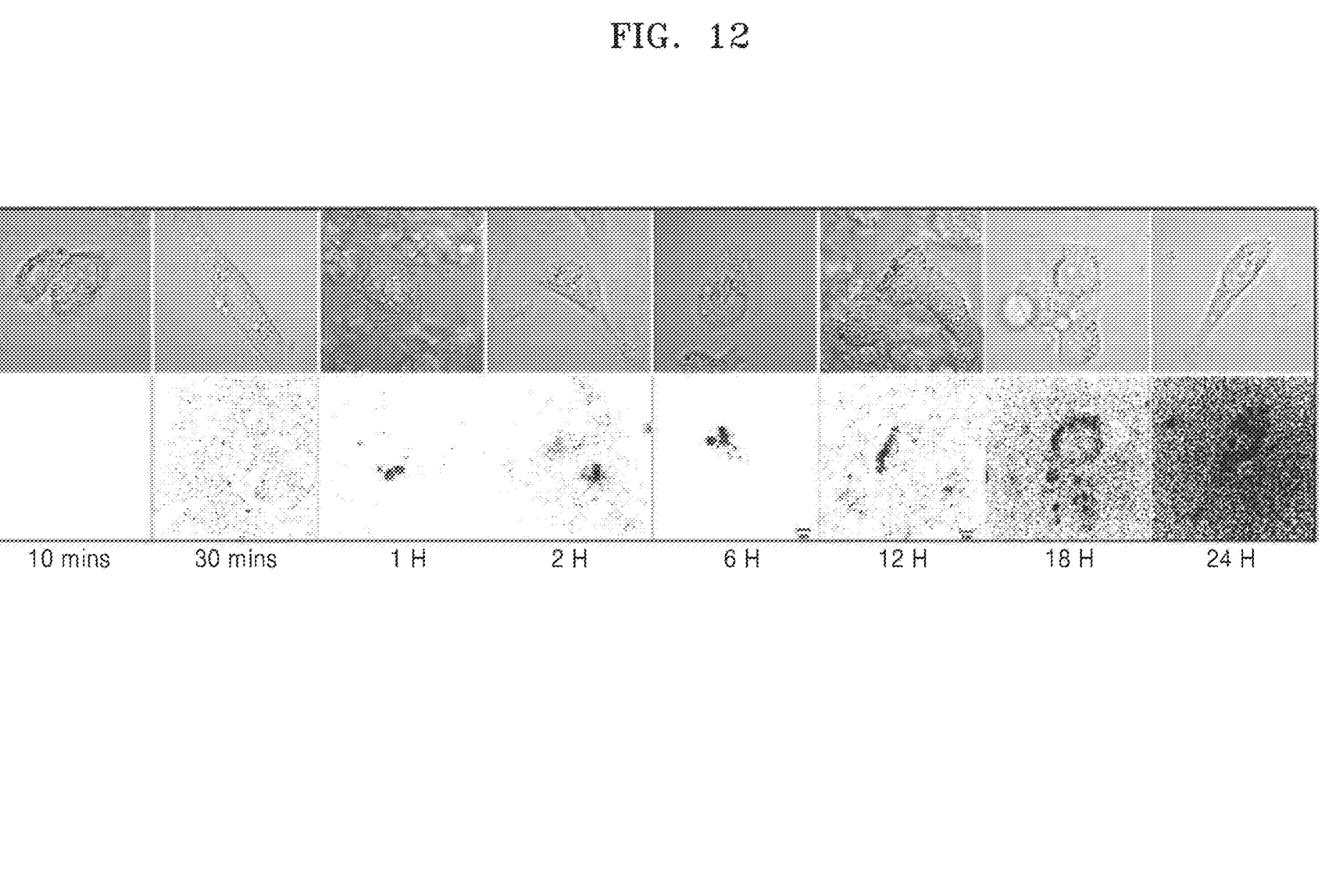
FIG. 12 shows reactions between cells and a nanoemulsion over time.
Figure 13:
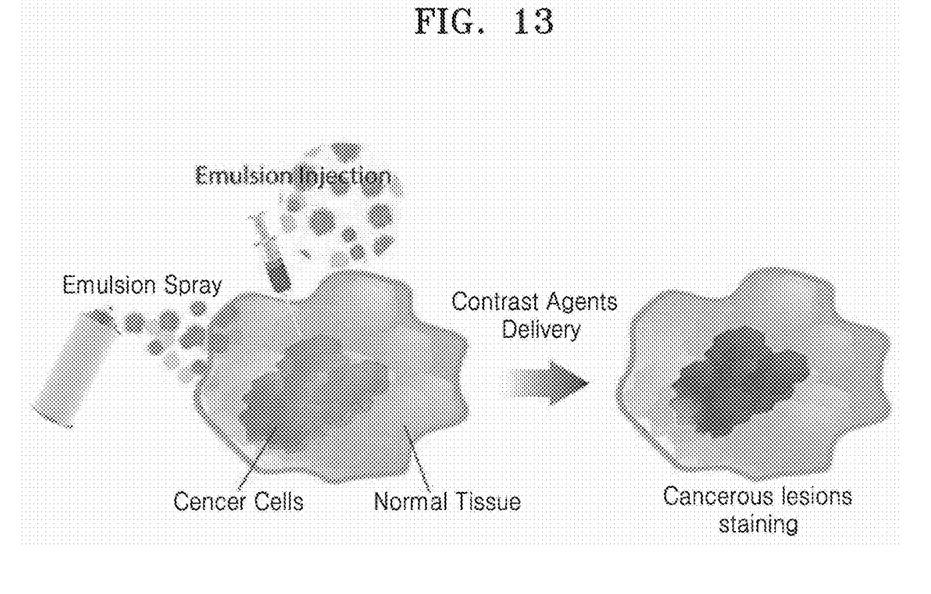
FIG. 13 illustrates delivery of a staining agent for selective labelling of cancer by a nanoemulsion.

FIG. 12 shows reactions between cells and nanoemulsion over time. The results of FIG. 12 confirmed that a staining agent for cancer labeling of human body may be effectively delivered over time.

In the method of preparing the nanoemulsion, the oil component, the surfactant, and the aqueous component are the same as described above.

MODE OF DISCLOSURE

Example

Hereinafter, the present disclosure will be described in more detail with reference to Examples. However, Examples according to the present disclosure may be modified in many different forms and should not be construed as being limited to Examples set forth herein. Rather, Examples of the present disclosure are provided to fully convey more thorough and complete explanation of this disclosure to those of ordinary skill in the art.

Preparation Example 1. Preparation of Nanoemulsion 1

Hyaluronic acid (Research grade from Lifecore, MW=41-65 kDa) and purified soybean oil (Sigma) were prepared. A methylene blue solution (Sigma) certified for microscopy by the Biological Staining Commission (BSC) was prepared. Span 80 (HLB value 4.3: Sigma) and Tween 80 (HLB value 15: Sigma) which are surfactants suitable for cell culture were prepared. Surfactants having different hydrophilic-lipophilic balance values as shown in the following Table were prepared by controlling a weight ratio of Span 80 to Tween 80.

An oil component (soybean oil) containing the prepared surfactant, a first aqueous component (0.5% sodium alginate and 0.5% sodium hyaluronate (w/w)), and a second aqueous component (contrast agent: 10 mM methylene blue solution or 10 mM indigo carmine solution) were prepared, respectively.

A mixed solution containing the oil component:surfactant:first aqueous component:second queous component at a weight ratio of 70:10:10:10 was stirred and mixed by sonication (Sonic, VC-505 model, amplitude: 20%) for 10 minutes to prepare a nanoemulsion.

After sonication until the blue mixture became transparent or translucent, a resulting product of the oil component was redispersed in deionized water (DI water) while the nanoemulsion being separated from the oil component. The aqueous component including nanoparticles was filtered using a cellulose acetate syringe filter (model DISMIC-13 from Advantec).

Preparation Example 2. Preparation of Nanoemulsion 2

A nanoemulsion was prepared in the same manner as in Preparation Example 1, except that the weight ratio of oil component:surfactant:aqueous component was controlled at 8:1:1 instead of 7:1:2 in Preparation Example 1.

Experimental Example 1

Particle size, particle size distribution (PDI), and zeta potential of the nanoemulsions prepared in Preparation Examples 1 and 2 were measured using a nanoparticle analyzer (Dynamic light scattering), and results are shown in Table 1 below.

TABLE 1

| Sample | Co-surfactant HLB value | oil component/ surfactant/aqueous component ratio(wt %) | Day 0 Size (nm, DLS Z-avg) | PDI | ZP (mV) |
| --- | --- | --- | --- | --- | --- |
| NE a | 5 | 7:1:2 | 88.62 ± 7.01 | 0.650 ± 0.10 | −22.22 ± 0.71 |
| NE b | 6 | | 12.10 ± 17.68 | 0.448 ± 0.12 | −46.01 ± 0.44 |
| NE c | 7 | | 15.18 ± 0.90 | 0.417 ± 0.06 | −22.24 ± 0.58 |
| NE d | 8 | | 42.12 ± 23.53 | 0.418 ± 0.05 | −24.64 ± 0.39 |
| NE e | 5 | 8:1:1 | 59.12 ± 18.25 | 0.588 ± 0.06 | −43.30 ± 0.26 |
| NE f | 6 | | 55.96 ± 29.71 | 0.312 ± 0.03 | −46.17 ± 0.35 |
| NE g | 7 | | 44.69 ± 22.78 | 0.295 ± 0.03 | −44.20 ± 0.72 |
| NE h | 8 | | 61.25 ± 16.6 | 0.536 ± 0.13 | −27.77 ± 0.25 |

The results of Table 1 showed that the size of nanoemulsion may be controlled by controlling the hydrophilic-lipophilic balance values of the nanoemulsions.

Preparation Example 3. Preparation of Nanoemulsion 3

A nanoemulsion was prepared using oil component:surfactant:aqueous component at a weight ratio of 7:1:2 in the same manner as in Preparation Example 1, except that hyaluronic acid having a higher average molecular weight (MW=91-175 kDa) was used in Preparation Example 1. Results of measuring changes in the particle size and zeta potential according to concentrations of sodium alginate and sodium hyaluronate which correspond to the first aqueous component, and changes in the particle size and zeta potential according to the concentration of methylene blue are shown in Tables 2 and 3, below

TABLE 2

| Sample | Oily phase | Co-surfactant (Span 80/Tween 80) | Aqueous phase |
| --- | --- | --- | --- |
| NE 1 | 3.5 | 0.42/0.08 | 0.4/0.4/0.2 = HA 1 wt %/Alg 1 wt %/MB 10 mM |
| NE 2 | 3.5 | 0.37/0.13 | 0.4/0.4/0.2 = HA 1 wt %/Alg 1 wt %/MB 10 mM |
| NE 3 | 3.5 | 0.32/0.18 | 0.4/0.4/0.2 = HA 1 wt %/Alg 1 wt %/MB 10 mM |
| NE 4 | 3.5 | 0.28/0.22 | 0.4/0.4/0.2 = HA 1 wt %/Alg 1 wt %/MB 10 mM |

TABLE 2-continued

| Sample | Oily phase | Co-surfactant (Span 80/Tween 80) | Aqueous phase |
|---|---|---|---|
| NE 5 | 3.5 | 0.42/0.08 | m.25/0.25/0.5 = HA 1 wt %/Alg 1 wt %/MB 10 mM |
| NE 6 | 3.5 | 0.37/0.13 | m.25/0.25/0.5 = HA 1 wt %/Alg 1 wt %/MB 10 mM |
| NE 7 | 3.5 | 0.32/0.18 | m.25/0.25/0.5 = HA 1 wt %/Alg 1 wt %/MB 10 mM |
| NE 8 | 3.5 | 0.28/0.22 | m.25/0.25/0.5 = HA 1 wt %/Alg 1 wt %/MB 10 mM |
| NE 9 | 3.5 | 0.42/0.08 | 0.25/0.25/0.5 = HA 0.5 wt %/Alg 0.5 wt %/MB 1 mM |
| NE 10 | 3.5 | 0.37/0.13 | 0.25/0.25/0.5 = HA 0.5 wt %/Alg 0.5 wt %/MB 1 mM |
| NE 11 | 3.5 | 0.32/0.18 | 0.25/0.25/0.5 = HA 0.5 wt %/Alg 0.5 wt %/MB 1 mM |
| NE 12 | 3.5 | 0.28/0.22 | 0.25/0.25/0.5 = HA 0.5 wt %/Alg 0.5 wt %/MB 1 mM |

TABLE 3

| | Co-surfactant HLB value | DAY 0 Size (nm, DLS Z-avg) | DAY 0 PDI | DAY 7 Size (nm, DLS Z-avg) | DAY 7 PDI | ZP (mV) |
|---|---|---|---|---|---|---|
| NE 1  | 6 | 208.4 ± 1.4 | 0.208 ± 0.015 | 227.2 ± 3.4 | 0.238 ± 0.007 | −46.2 ± 8.7 |
| NE 2  | 7 | 196.8 ± 2.8 | 0.239 ± 0.013 | 246.2 ± 6.3 | 0.284 ± 0.010 | −30.0 ± 1.8 |
| NE 3  | 8 | 114.5 ± 3.4 | 0.265 ± 0.002 | 114.5 ± 3.8 | 0.445 ± 0.029 | −30.3 ± 0.2 |
| NE 4  | 9 | 42.1 ± 4.3 | 0.683 ± 0.132 | 86.0 ± 0.9 | 0.592 ± 0.001 | −35.4 ± 0.4 |
| NE 5  | 6 | 142.2 ± 0.5 | 0.194 ± 0.009 | 149.5 ± 1.2 | 0.235 ± 0.001 | −38.4 ± 2.7 |
| NE 6  | 7 | 157.3 ± 3.1 | 0.313 ± 0.003 | 157.8 ± 1.5 | 0.325 ± 0.052 | −31.2 ± 2.4 |
| NE 7  | 8 | 149.5 ± 6.5 | 0.306 ± 0.042 | 162.8 ± 2.3 | 0.250 ± 0.009 | −33.6 ± 0.8 |
| NE 8  | 9 | 184.3 ± 4.7 | 0.359 ± 0.045 | 176.0 ± 2.4 | 0.301 ± 0.035 | −28.4 ± 1.3 |
| NE 9  | 6 | 158.0 ± 1.6 | 0.147 ± 0.015 | 160.9 ± 1.8 | 0.124 ± 0.027 | −31.9 ± 1.8 |
| NE 10 | 7 | 125.9 ± 2.6 | 0.284 ± 0.006 | 127.4 ± 2.6 | 0.269 ± 0.005 | −33.4 ± 0.7 |
| NE 11 | 8 | 38.4 ± 0.4 | 0.503 ± 0.003 | 47.2 ± 0.6 | 0.597 ± 0.005 | −33.7 ± 1.0 |
| NE 12 | 9 | 47.3 ± 0.8 | 0.622 ± 0.009 | 64.6 ± 2.5 | 0.648 ± 0.032 | −23.5 ± 2.1 |

The results of Tables 2 and 3 showed that the particle size depends on the hydrophilic-lipophilic balance value of the nanoemulsion, which are consistent with the results of Table 1. Further, the particle size and stability depend on concentrations of the first aqueous component and the second aqueous component (sodium alginate, sodium hyaluronate, and methylene blue).

While the present disclosure has been described with reference to preferred embodiments, it will be understood by those skilled in the art that the present disclosure may be implemented in a modified form without departing from the essential characteristics thereof. Therefore, it should be understood that embodiments described herein should be considered in a descriptive sense only and not for purposes of limitation. The scope of the present disclosure is defined by the appended claims rather than by the foregoing description, and all differences within the scope of equivalents thereof should be construed as being included in the present disclosure.

What is claimed is:

1. A nanoemulsion comprising an oil component; a surfactant; and an aqueous component, wherein the aqueous component comprises a water-soluble active ingredient comprising water-soluble stain or a water-soluble drug; a polysaccharide; and a hyaluronic acid; and the oil component is soybean oil;
   wherein the nanoemulsion has an average particle size of 200 nm or less, and the nanoemulsion is a water-in-oil-type emulsion,
   wherein the nanoemulsion comprises 70% by weight to 80% by weight of the oil component, 10% by weight to 20% by weight of the aqueous component, and 5% by weight to 15% by weight of the surfactant, based on the total weight of the nanoemulsion; and
   wherein the polysaccharide is alginate.

2. The nanoemulsion of claim 1, wherein the nanoemulsion comprises an interpenetrating polymer network structure consisting of the water-soluble active ingredient, the polysaccharide, and the hyaluronic acid.

3. The nanoemulsion of claim 1, wherein the surfactant comprises at least one of a single surfactant or a co-surfactant.

4. The nanoemulsion of claim 1, wherein nanoparticles comprised in the nanoemulsion have an average polydispersity index (PDI) of 0.2 to 0.7 and a zeta potential of −20 mV to −50 mV.

5. The nanoemulsion of claim 1, wherein the water-soluble stain is any one selected from the group consisting of indigo carmine, methylene blue, Lugol solution, toluidine blue, congo red, phenol red, indocyanine green, fluorescein sodium, and india ink.

6. The nanoemulsion of claim 1, wherein a concentration of the water-soluble stain is 1 mM to 10 mM.

7. The nanoemulsion of claim 1, wherein a hydrophilic-lipophilic balance value of the nanoemulsion is 6 to 9.

8. A method of preparing the nanoemulsion of claim 1, the method comprising:
   preparing the oil component comprising soybean oil;
   preparing the surfactant;
   preparing the aqueous component; and
   mixing and stirring the oil component, the surfactant, and the aqueous component, wherein the aqueous component comprises the water-soluble active ingredient comprising water-soluble stain or a water-soluble drug, the polysaccharide, and the hyaluronic acid,
   and the nanoemulsion comprises 70% by weight to 80% by weight of the oil component, 10% by weight to 20% by weight of the aqueous component, and 5% by weight to 15% by weight of the surfactant, based on the total weight of the nanoemulsion, and the nanoemulsion has an average particle size of 200 nm or less, and the nanoemulsion is a water-in-oil-type emulsion.

9. The method of preparing the nanoemulsion of claim 8, wherein the preparing of the aqueous component comprises preparing a first aqueous component including the polysaccharide and the hyaluronic acid; and preparing a second aqueous component including the water-soluble active ingredient comprising water-soluble stain or a water-soluble drug.

10. The method of preparing the nanoemulsion of claim 9, wherein a weight ratio of the first aqueous component to the second aqueous component is 1:0.5 to 1:2.

* * * * *